United States Patent [19]

Coon et al.

[11] Patent Number: 4,469,898
[45] Date of Patent: * Sep. 4, 1984

[54] METHOD OF SYNTHESIZING FLUOROMETHYLHEXAFLUOROISOPROPYL ETHER

[75] Inventors: Clifford L. Coon, Fremont; Robert L. Simon, San Carlos, both of Calif.

[73] Assignee: Baxter Travenol Laboratories, Inc., Deerfield, Ill.

[*] Notice: The portion of the term of this patent subsequent to Feb. 10, 1998 has been disclaimed.

[21] Appl. No.: 446,930

[22] Filed: Dec. 6, 1982

Related U.S. Application Data

[63] Continuation of Ser. No. 291,881, Aug. 10, 1981, abandoned, which is a continuation-in-part of Ser. No. 107,117, Dec. 26, 1979, Pat. No. 4,250,334.

[51] Int. Cl.$^3$ .................. C07C 41/01; C07C 41/42
[52] U.S. Cl. ................................ 568/683; 568/682
[58] Field of Search ........................... 568/683, 682

[56] References Cited

U.S. PATENT DOCUMENTS 4,250,334  2/1981  Coon et al. .

OTHER PUBLICATIONS

Olah, Friedel–Crafts and Related Reactions, Interscience Publishers, New York, 1963, pp. 173, 348, 201–203.

Primary Examiner—Howard T. Mars
Attorney, Agent, or Firm—Garrettson Ellis; Paul C. Flattery

[57] ABSTRACT

A method of synthesizing fluoromethylhexafluoroisopropyl ether, comprising mixing hexafluoroisopropyl alcohol, formaldehyde, hydrogen fluoride, and a protonating, dehydrating and fluoride ion-generating agent under conditions suitable to generate fluoromethylhexafluoroisopropyl ether, and then recovering the fluoromethylhexafluoroisopropyl ether.

13 Claims, 1 Drawing Figure

METHOD OF SYNTHESIZING FLUOROMETHYLHEXAFLUOROISOPROPYL ETHER

RELATED COPENDING APPLICATION

This is a continuation of application Ser. No. 291,881, filed Aug. 10, 1981, now abandoned, which is a continuation-in-part of U.S. patent application Ser. No. 107,117, filed Dec. 26, 1979 now U.S. Pat. No. 4,250,334.

BACKGROUND OF THE INVENTION

Fluoromethyl-1,1,1,3,3,3-hexafluoroisopropyl ether, as described in U.S. Pat. Nos. 3,683,092 and 3,689,571, is a promising new anesthetic for human use which is essentially non-inflammable, and appears to have few or no undesirable side effects when administered to humans.

In the abandoned patent application Ser. No. 771,365, filed Oct. 28, 1978, from which the above two patents claim priority, several techniques are suggested which may be used for making ethers having halogen groups in both of the organic ether substituents, including fluoromethylhexafluoroisopropyl ether. It is suggested there that the corresponding alcohol may be reacted with formaldehyde and hydrogen fluoride to form the fluoromethyl ether. However, yields of this reaction generally described in the abandoned patent application cited above, are not of a desired commercial scale, so other, more cumbersome, multiple step synthesis routes were initially preferred. Weynmayr U.S. Pat. No. 2,992,276 also teaches the use of paraformaldehye and hydrogen fluoride as a reagent for synthesizing a fluoromethylether and an alcohol from tetrafluoroethylene.

In accordance with this invention, a simplified, high yield synthesis technique for fluoromethylhexafluoroisopropyl ether is disclosed, capable of producing yields of the desired ether product of the order of 90 percent, with recycling of unused reactants through the reaction mixture for optimization of synthesis. Particularly, fluoromethyl-1,1,1,3,3,3-hexafluoroisopropyl ether may be made this way as a clinical anesthetic on a large scale basis.

SUMMARY OF THE INVENTION

In accordance with this invention, fluoromethylhexafluoroisopropyl ether may be synthesized by mixing hexafluoroisopropyl alcohol, formaldehyde, hydrogen fluoride, and a protonating, dehydrating and fluoride ion-generating agent under conditions suitable to generate fluoromethylhexafluoroisopropyl ether, and then recovering the fluoromethylhexafluoroisopropyl ether.

BRIEF DESCRIPTION OF THE DRAWING

Referring to FIG. 1, reaction vessel 10, made of Kel-F fluorinated plastic and sealed with closure 12, defines an inlet line 14 which has a branch connection. One of the connection 16 is connected to a source of pressurized inert, e.g., nitrogen gas, and the other connection 18 is connected to a source of hexafluoroisopropyl alcohol. The reaction vessel 10 is equipped with a magnetic stirring bar 20, and positioned within an oil bath 22 for control of the temperature of the reaction mixture at, preferably, about 65° C.

Figure 1:
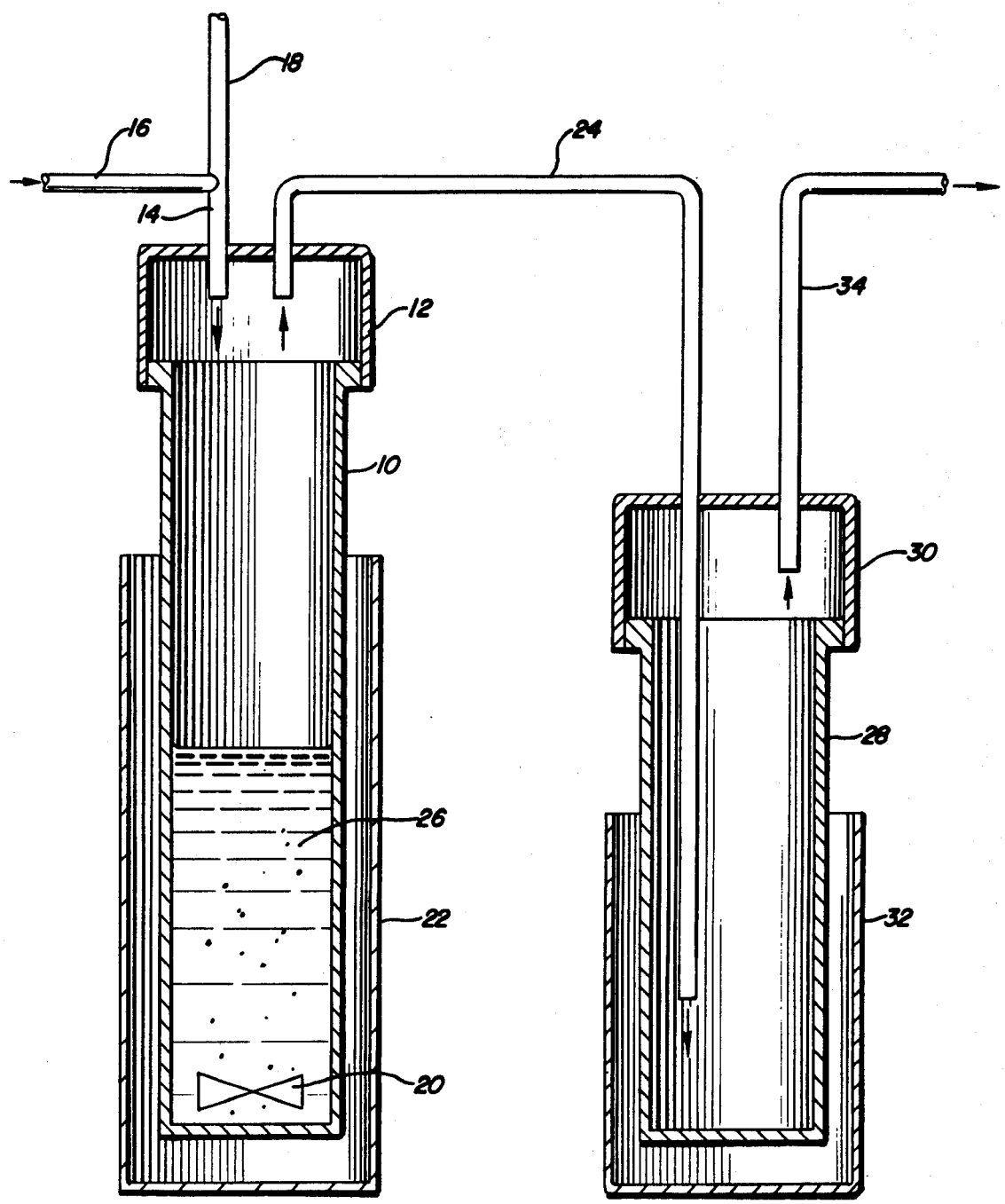
FIG. 1 is a schematic view of the reaction apparatus used for performing the reaction described above, with further details of the reaction technique added.

Tubular outlet line 24 communicates with container 10 and carries vapors generated by the reaction mixture 26, to a collector container 28 made of Kel-F fluorinated plastic. Container 28 also defines closure 30 with line 34 sealingly passing through it. Container 28 is also placed in a cooling bath 32 to assist in condensation of the vapors in container 32.

Vent line 34 communicates with the exterior. Accordingly, nitrogen gas may be constantly used to provide a low velocity gas sweep through the reaction system, while the alcohol reactant is added dropwise through inlet line 18. The vapors which are generated leave reaction chamber 10 through line 24, and are condensed in container 28. The sweeping nitrogen gas then continues to pass outwardly through vent 34, while the products and byproducts of the reaction are collected in the collector container 28.

DETAILED DESCRIPTION OF THE PREFERRED EMBODIMENTS

While the order of addition of reactants is not critical, the synthesis is preferably conducted by slowly adding the hexafluoroisopropyl alcohol to a preformed mixture of formaldehyde, hydrogen fluoride and the dehydrating, protonating and fluoride ion-generating agent.

The identity of the selected agent is not critical so long as the protonating, dehydrating and fluoride ion-generating functions are accomplished to at least some degree in the reaction mixture. As a principal feature, the agent must be capable of sequestering water generated during the reaction. The effectiveness of a proposed agent for such purpose may be readily determined in a pilot synthesis by simply assaying for the presence of free water in the reaction mixture.

The agent should also be a proton donating agent in the reaction of hexafluoroisopropyl alcohol with formaldehyde and hydrogen fluoride, and should generate fluoride ions in the same reaction. Agents which exhibit these characteristics enhance yields to greater than about 40% fluoromethylhexafluoroisopropyl ether based on the weight of the alcohol starting material.

Suitable agents include Brönsted acids having a relative acid strength in excess of about 15 for the first proton, in particular sulfuric acid (relative strength 39), flurosulfonic acid or trifluoromethanesulfonic acid (both 427). Lewis acids such as titanium or aluminum tetrachloride, aluminum trifluoride or antimony pentafluoride are also useful. Brönsted acids are on balance preferred. Mixtures may also be employed; sulfuric acid or a mixture of fluorosulfonic acid and sulfuric acid have produced the best yields to date.

The term "formaldehyde" as used herein is intended to include formaldehyde polymers such as paraformaldehyde, which is preferred.

The reaction temperature is not critical, but yields are considerably improved above about 50° C. Preferably, the temperature of the reaction mixture is maintained at about 57 to 70 degrees, with the hexafluoroisopropyl alcohol being added on a continuous, gradual basis. This permits the distillation of the ether product concurrent with its synthesis, thereby reducing degradation of the product when exposed to the harsh conditions of the reaction mixture.

Both the formaldehyde and the hydrogen fluoride are present optimally in a stoichiometric excess compared to the total amount of alcohol to be used. Preferably, at least about from 10 to 100 percent molar excess of formaldehyde and at least about from 400 to 1000 percent excess of hydrogen fluoride are present in the reaction mixture.

It is preferable that at least half again as much agent as formaldehyde by weight be present. Preferably, about from 50 to 200 percent greater weight of a Brönsted acid such as sulfuric acid will be employed.

The fluoromethylhexafluoroisopropyl ether is recovered from the reaction mixture in any known fashion, preferably by condensing vapors generated during the reaction. Recovery of product is aided by employing a reaction temperature in excess of about 57° C., the boiling point of fluoromethylhexafluoroisopropyl ether. A major proportion of the condensate is the starting alcohol and the ether product. It is preferably neutralized where a volatile acid had been used as the agent. The condensate can then be redistilled to improve the ether purity. A fraction distilling at about from 58° C. to 95° C. principally contains the alcohol starting material, while distillation at a temperature below about 58° will yield the ether. The alcohol-containing fraction may be recycled to the reaction mixture. Thus, the process may be conducted continuously if the recycled fraction, formaldehyde, hydrogen fluoride and supplementary starting alcohol are added as required.

It is contemplated that other ingredients such as solvents, catalysts, diluents, and other materials may also be present in the reaction mixture if desired, as long as the added extraneous materials do not materially change the nature of the reaction described above, but are added to promote the reaction, suppress side reactions, or improve the purification step of the synthesis.

The following examples are presented for illustrative purposes only, and are not intended to limit the scope of the invention, which is as defined in the claims below. All analyses were conducted by gas chromatography. All percentages are by weight.

EXAMPLE 1—SULFURIC ACID SYSTEM 5 ml. of 96% sulfuric acid and 10 grams (0.5 mole) of hydrogen fluoride were added to 3.0 grams (0.1 mole of paraformaldehyde. This reaction mixture was heated to 65° C. Thereafter, 13.4 grams (0.08 mole) of 1,1,1,3,3,3-hexafluoroisopropyl alcohol was added drop-by-drop over one hour. The reaction was conducted in the device described above and shown in FIG. 1. During this period, vapors were generated during the dropwise addition of the alcohol reactant. These vapors were collected in a cooled collector of a distillation set over a period of two hours, using the nitrogen sweep technique and apparatus shown in FIG. 1. Thereafter, the material obtained in the cooled collector at the end of the two hours was quenched on ice, neutralized with ammonia, and distilled.

The material from the cooled collector gave two fractions on distillation. Fraction 1, distilling between 25° and 58° C., provided 6.7 grams of material containing 90% fluoromethyl-1,1,1,3,3,3-hexafluoroisopropyl ether, 3% of the initial alcohol reaction material, and 7% of a formal byproduct.

Fraction 2 from the cooled collector, distilling between 58° and 95° C., yielded 5.5 grams of material containing 11% fluoromethyl-1,1,1,3,3,3-hexafluoroisopropyl ether, 42% of the alcohol starting material, 33% of a formal byproduct, and 13% of an acetal byproduct.

EXAMPLE 2—PHOSPHORIC ACID SYSTEM

Paraformaldehyde (13 gram), phosphoric acid (103 gram), hydrogen fluoride (75 gram) and hexafluoroisopropanol (47 gram) were combined in the FIG. 1 reactor and heated at 65° C. for three hours. The distilled vapors were collected and neutralized with excess ammonia. The collected product (23 gram) contained 88% hexafluoroisopropyl alcohol, 4.5% bishexafluoroisopropyl dioxymethylene acetal, 5% methyl hexafluoroisopropyl ether and 0.05% fluoromethyl-1,1,1,3,3,3-hexafluoroisopropyl ether. Phosphoric Acid is a Brönsted acid having an acid equivalent number of −1.6.

EXAMPLE 3—TRIFLUOROMETHANESULFONIC ACID SYSTEM

Paraformaldehyde (13 gram), trifluoromethanesulfonic acid (39 gram), hydrogen fluoride (43 gram) and hexafluoroisopropyl alcohol (44 gram) were combined in the FIG. 1 reactor and heated at 65° C. for three hours. The distilled vapors were collected and neutralized with excess ammonia. The isolated product (30 gram) contained 66% fluoromethyl-1,1,1,3,3,3-hexafluoroisopropyl ether and 26% hexafluoroisopropyl alcohol.

EXAMPLE 4—SULFURIC ACID SYSTEM

Paraformaldehyde (13 gram), concentrated sulfuric acid (136 gram), hydrogen fluoride (53 gram) and hexafluoroisopropyl alcohol (44 gram) were combined in the FIG. 1 reactor and heated at 65° for three hours. The distilled vapors were collected and neutralized with excess ammonia. The isolated product (48 gram) contained 84% fluoromethyl-1,1,1,1,3,3,3-hexafluoroisopropyl ether.

EXAMPLE 5—FLUOROSULFONIC/SULFURIC ACID SYSTEM

Paraformaldehyde (13 gram), concentrated sulfuric acid (50 gram), 20% sulfur trioxide in sulfuric acid (100 gram), hydrogen fluoride (58 gram) and hexafluoroisopropyl alcohol (45 gram) were combined in the FIG. 1 reactor and heated at 65° C. for three hours. The distilled vapors were collected and neutralized with excess ammonia. The isolated product (45.5 gram) contained 90% fluoromethyl-1,1,1,3,3,3-hexafluoroisopropyl ether.

What is claimed is:

1. The method of synthesizing fluoromethylhexafluoroisopropyl ether, comprising mixing hexafluoroisopropyl alcohol, formaldehyde, hydrogen fluoride, and a protonating, dehydrating and fluoride ion-generating agent under conditions suitable to generate fluoromethylhexafluoroisopropyl ether, and recovering the fluoromethylhexafluoroisopropyl ether.

2. The method of claim 1 wherein the fluoromethylhexafluoroisopropyl ether is recovered by distillation of the reaction mixture.

3. The method of claim 1 wherein the formaldehyde is paraformaldehyde.

4. The method of claim 1 in which the mixture is maintained at a temperature of at least about 50° C.

5. The method of claim 4 wherein the temperature is at least about 57° C.

6. The method of claim 4 wherein the temperature is about from 60° to 70° C.

7. The method of claim 1 in which said hexafluoroisopropyl alcohol is added to the reaction mixture at approximately the same rate that fluoromethylhexafluoroisopropyl ether is recovered from the reaction mixture.

8. The method of claim 1 in which at least a 10% molar excess of formaldehyde is present, based on the hexafluoroisopropyl alcohol added.

9. The method of claim 1 in which at least a 400% molar excess of hydrogen fluoride is present, based on the hexafluoroisopropyl alcohol added.

10. The method of claim 1 in which from 10 to 100 molar % excess formaldehyde and 400 to 1000 molar % excess of hydrogen fluoride is present.

11. The method of claim 2 wherein the recovered ether is further purified by distillation and the residue recycled to the reaction mixture.

12. The method of synthesizing fluoromethylhexafluoroisopropyl ether, comprising mixing hexafluoroisopropyl alcohol, formaldehyde, hydrogen fluoride and a Lewis acid under conditions suitable to generate fluoromethylhexafluoroisopropyl ether, and recovering the fluoromethylhexafluoroisopropyl ether.

13. The method of claim 12 wherein the Lewis acid is titanium tetrachloride, aluminum tetrachloride, aluminum trifluoride or antimony pentafluoride.

* * * * *